United States Patent [19]
Brunner et al.

[11] Patent Number: 5,622,845
[45] Date of Patent: Apr. 22, 1997

[54] FERMENTATION METHOD FOR PRODUCING NORLEUCINE

[75] Inventors: David P. Brunner, Portage; Gary C. Harbour; Richard J. Kirschner, both of Kalamazoo; James F. Pinner, Portage; Robert L. Garlick, Augusta, all of Mich.

[73] Assignee: The Upjohn Company, Kalamazoo, Mich.

[21] Appl. No.: 470,683

[22] Filed: Jun. 6, 1995

Related U.S. Application Data

[60] Division of Ser. No. 566,442, Aug. 17, 1990, which is a continuation-in-part of Ser. No. 157,275, Feb. 17, 1988, abandoned.

[51] Int. Cl.$^6$ .............................. C12N 1/20; C12P 13/04; C12P 13/06
[52] U.S. Cl. .................. 435/106; 435/113; 435/116; 435/252.33; 435/252.8; 435/849
[58] Field of Search ........................... 435/106, 113, 435/252.33, 252.8, 849, 116

[56] References Cited

U.S. PATENT DOCUMENTS

| | | | |
|---|---|---|---|
| 4,562,175 | 12/1985 | Chang et al. | 514/12 |
| 4,731,440 | 3/1988 | Bentle et al. | 530/399 |

FOREIGN PATENT DOCUMENTS 0209355  1/1987  European Pat. Off. .

OTHER PUBLICATIONS

J.S. Harris and H.I. Kohn, J. Pharmacol., 73, pp. 383–400 (1941).
J.O. Lampen and M.J. Jones, Arch. Biochem. Biophys., 13, pp. 47–53 (1947).
R. Munier and G.N. Cohen, Biochim. Biophys. Acta., 31, pp. 378–390 (1959).
D.G. Barker and C.J. Bruton, J. Mol. Biol., 133, pp. 217–231 (1979).
B. Nisman and M.L. Hirsch, Ann. Inst. Pasteur, 95, pp. 615–634 (1958).
J.M. Old and D.S. Jones, Biochem. J., 165, pp. 367–373 (1977).
J. Trupin et al., Biochem. Biophys. Res. Comm., 24, pp. 50–55 (1966).
A.R. Fersht and C. Dingwall, Biochem., 18, pp. 1250–1256 (1979).
S.S. Kerwar and H. Weissbach, Arch. Biochem. Biophys., 141, pp. 525–532 (1970).
E. Abderhalden and K. Heyns, Zwitschr. Physiol. Chem., 214, pp. 262–266 (1933).
R. Nuccorini, Ann. Chim. Appl., 24, pp. 25–32 (1934).
P. Nandi and G.P. Sen, Nature, 171, pp. 871–872 (1953).
M. Kisumi, et al., J. Biochem., 80, pp. 333–339 (1976).
M. Kisumi et al., Appl. Environ. Microbiol., 34, pp. 135–138 (1977).
George, H.J. et al., "High–Level Expression in *Escherichia coli* of Biologically Active Bovine Growth Hormone," DNA, 4(4):273–281 (1985).
Tokunaga, T. et al., "Expression of a synthetic human growth hormone gene in yeast," Gene, 39:117–120 (1985).
Cohen, G.N. et al., "Biosynthesis of Threonine, Lysine, and Methionine," in Escherichia and Salmonella Typhimurium, F.C. Neidhardt, ed. 429–444 (1987).
Naider, F., et al., "Reversible Alkylation of a Methionyl Residue near the Active Site of β–Galactosidase," Biochemistry, 11, pp. 3202–3208 (1972).
Barker, D.G. and Bruton, C.J., "The Fate of Norleucine as a Replacement for Methionine in Protein Synthesis," J. Mol. Biol., 133, pp. 217–231 (1979).
Brown, J.L., "The Modification of the Amino Terminal Region of *Escherichia coli* Proteins After Initiation with Methionine Analogues," Biochemica et Biophysica Acta, 294, pp. 527–529 (1973).
Tsai, L.B., et al., "Control of Misincorporation of De Novo Synthesized Norleucine into Recombinant Interleukin–2 in *E. coli*," Biochemical and Biophysical Research Communications, 156, pp. 733–739 (1988).
Gilles, A.M., et al., "Conservative Replacement of Methionine by Norleucine in *Escherichia coli* Adenylate Kinase," J. Biol. Chem., 263, pp. 8204–8209 (1988).
Bogosian, G., et al., "Biosynthesis and Incorporation into Protein of Norleucine by *Escherichia coli*," J. Biol. Chem., 264, pp. 531–539 (1989).

*Primary Examiner*—Dian C. Jacobson
*Attorney, Agent, or Firm*—James D. Darnley, Jr.; Paul J. Koivuniemi

[57] ABSTRACT

The present invention provides an inexpensive fermentation medium for growing microorganisms. Also provided are fermentation media and methods for producing norleucine by growing *E. coli* thereon, fermentation media and methods for incorporating norleucine into polypeptides expressed by microorganisms grown thereon, and fermentation media and methods for preventing the incorporation of norleucine into polypeptides expressed by microorganisms grown thereon. Also provided are bovine somatotropin analogs.

1 Claim, No Drawings

FERMENTATION METHOD FOR PRODUCING NORLEUCINE

CROSS-REFERENCE TO RELATED APPLICATIONS

This application is a divisional of U.S. Ser. No. 07/566,442, filed 17 Aug. 1990; which is a continuation of International Patent Application No. PCT/US89/00425, filed 7 Feb. 1989; which is a continuation-in-part of U.S. Ser. No. 07/157,275, filed 17 Feb. 1988, abandoned.

FIELD OF INVENTION

This invention is in the field of biochemical engineering. More particularly, this invention relates to fermentation processes for producing polypeptides and the polypeptides produced thereby.

BACKGROUND OF THE INVENTION

Synthetic and chemically defined media for cultivating microorganisms are well known. Conventional nutrient media for cultivating bacteria have been used to grow recombinant bacteria that are capable of producing heterologous polypeptides. Sources of amino acids such as yeast extract and casamino acids are usually included in high concentrations in the fermentation medium throughout the cultivation period. Such amino acids are expensive. Therefore it would be helpful to decrease the amount of supplemented amino acids in the fermentation medium while at the same time keeping expression of good quality desirable polypeptides at a high level.

INFORMATION DISCLOSURE

Norleucine is known to act as an analog of methionine in microbial metabolism. *E. coli* growth has been reported to be prevented by competitive inhibition of methionine utilization by supplying exogenous norleucine (J. S. Harris and H. I. Kohn, J. Pharmacol., 73, pp. 383–400 (1941)). Norleucine supplementation has also been observed to increase the growth of an *E. coli* methionine auxotroph in media containing suboptimal concentrations of methionine (J. O. Lampen, and M. J. Jones. Arch. Biochem. Biophys., 13, pp. 47–53 (1947)). However, studies examining the biological roles of norleucine have only employed norleucine supplied as an exogenous amino acid source.

R. Munier and G. N. Cohen, Biochim. Biophys. Acta., 31, pp. 378–90 (1959) showed that exogenously-supplied norleucine could be incorporated in vivo into bacterial proteins in place of methionine. Detailed studies on the fate of norleucine as a replacement for methionine in *E. coli* protein synthesis support the ability of norleucine to be incorporated into *E. coli* proteins (D. G. Barker and C. J. Bruton, J. Mol. Biol., 133, pp. 217–31 (1979)). Norleucine has been shown both in vitro and in vivo to be able to charge tRNA$^{Met}$ and tRNA$^{fMet}$. Norleucine has been shown to form an aminoacyl-adenylate complex and release $PP_i$ in the presence of methionyl-tRNA synthetase (ATP-$PP_i$ exchange reaction) (B. Nisman and M. L. Hirsch, Ann. Inst. Pasteur, 95, pp. 615–34 (1958); J. M. Old and D. S. Jones, Biochem. J., 165, pp. 367–73 (1977)). Norleucine has also been shown to substitute for methionine in the acylation of *E. coli* tRNA$^{Met}$ (J. Trupin et al., Biochem. Biophys. Res. Commun., 24, pp. 50–55 (1966); A. R. Fersht and C. Dingwall, Biochem., 18, pp. 1250–56 (1979)). In addition, norleucyl-tRNA$^{fMet}$ is readily formylated to formylnorleucyl-tRNA$^{fMet}$ and can substitute for formylmethionyl-tRNA$^{fMet}$ to initiate protein synthesis (S. S. Kerwar and H. Weissbach, Arch. Biochem. Biophys., 141, pp. 525–32 (1970)). It has also been shown that when methionine is depleted and norleucine is supplied, the percent total tRNA$^{Met}$ that is charged (almost exclusively with norleucine) is <50% of the total tRNA$^{Met}$ (Barker and Bruton, supra). Inhibition of growth by norleucine has been reported (R. Munier and G. N. Cohen, supra; S. S. Kerwar and H. Weissbach, supra; Barker and Bruton, supra).

Therefore, while norleucine has long been known to act as a methionine analog, through in vivo and in vitro experimentation with exogenously supplied norleucine, we are unaware of any reports regarding the synthesis of norleucine by *E. coli* cultures. Early reports have cited the natural presence of norleucine and a structurally related compound, norvaline. Norleucine was found in animal nerve tissue (E. Abderhalden and K. Heyns, Zwitschr. Physiol. Chem., 214, pp. 262–66 (1933)) and as a constituent of *Ricinus communis* seeds (R. Nuccorini, Ann. Chim. Appl., 24, pp. 25–32 (1934)), while norvaline has been reported to be a component of an antifungal protein synthesized by *Bacillus subtilis* (P. Nandi and G. P. Sen, Nature, 171, pp. 871–72 (1953)).

Formation of norleucine by complex regulatory mutants of *Serratia marcescens* has been reported (M. Kisumi, et al., J. Biochem., 80, pp. 333–39 (1976); M. Kisumi et al, Appl. Environ. Microbiol., 34, pp. 135–38 (1977)). A mutant of *S. marcescens* which was derepressed for the leucine biosynthetic enzymes was selected and used to further select an isoleucine-dependent mutant lacking threonine dehydratase. From this double mutant, an isoleucine-independent (threonine-dehydratase deficient) mutant which contained a feedback-resistant α-isopropylmalate synthase was selected. This final complex mutant accumulated norleucine.

SUMMARY OF THE INVENTION

The present invention relates generally to decreasing norleucine incorporation into polypeptides expressed by microorganisms grown on a fermentation medium comprising a low concentration of amino acids, which comprises either increasing the concentration of methionine or decreasing the amount of norleucine in the fermentation medium, or a combination of both.

More specifically, the present invention relates to a method to decrease norleucine incorporation into polypeptides expressed by microorganisms grown on a defined fermentation medium having a low concentration of amino acids, which comprises supplementing the medium with sources of methionine, cysteine, or leucine, or combinations thereof. Norleucine incorporation can be prevented by methionine or leucine supplementation.

More specifically, the microorganism is a recombinant microorganism and the polypeptide so expressed is a heterologous polypeptide.

The present invention also relates to a fermentation medium having a low concentration of amino acids and supplemented with sources of methionine, cysteine, or leucine, or combinations thereof.

The present invention also relates to methods for preventing norleucine incorporation into polypeptides expressed by microorganisms comprising utilizing a mutant microorganism able to overproduce methionine.

The present invention also relates to methods for incorporating norleucine into polypeptides expressed by microorganisms comprising growing said microorganism on a defined fermentation medium having a low concentration of amino acids and allowing protein overexpression.

The present invention also relates to methods for incorporating norleucine into polypeptides expressed by microorganisms comprising growing said microorganisms on a defined fermentation medium having a low concentration of methionine and supplemented with norleucine.

Also provided is a method for producing norleucine comprising growing *E. coli* on a fermentation medium having a low concentration of amino acids and then isolating the norleucine so produced.

Also provided are bSt-like compounds wherein the methionines located at amino acid residues 5, 124, 149 and 179 are replaced with a different amino acid residue particularly selected from the group consisting of leucine, valine or isoleucine.

The present invention also relates to a method for preventing norleucine incorporation into heterologous polypeptides, for example bovine somatotropin, expressed by microorganisms transformed with a recombinant DNA molecule encoding said polypeptide and grown on a low concentration of amino acids, comprising changing the codons encoding methionine in said DNA molecule encoding said polypeptide to those encoding a different amino acid, for example isoleucine.

DETAILED DESCRIPTION OF THE INVENTION

As used herein, "heterologous polypeptide(s)" refers to polypeptides not naturally synthesized by a transformed host microorganism of interest. For example, an *E. coli* may produce bovine or human somatotropin, insulin, interferon, etc. The polypeptides so produced are called "heterologous polypeptides". Of particular interest in the context of this invention are those heterologous polypeptides comprising methionine.

Due to the molecular heterogeneity of somatotropins, the position numbers of amino acid residues of the various somatotropins may differ. The term "native mammalian somatotropin" includes naturally occurring species. Chart 1 illustrates the specific amino acid residues of bSt that correspond to the position 5, 124, 149, and 179 residues modified by this invention. The numbering for other somatotropins may differ where other species or analogs are involved. Using the methionine 5, 124, 149 or 179 of the bSt set forth in Chart 1, those of ordinary skill in the art can readily locate corresponding amino acids in alternative animal somatotropins, for example, mammalian somatotropins, for example, methionine 5 of porcine somatotropin, or their analogs, to achieve the desired avoidance of norleucine incorporation and product uniformity of the instant invention.

As used herein, "a low concentration of amino acids" means a concentration that is low enough such that it can be reduced by a microorganism cultured thereon to a "minimal concentration of amino acids", which is in turn defined as the concentration of exogenous amino acids which is too low to repress the biosynthesis of, or feedback inhibit effectively the activities of, amino acid biosynthetic enzymes (for example, leucine biosynthetic enzymes). Otherwise defined, "a low concentration of amino acids" means a concentration that can be reduced by a microorganism cultured thereon to a "minimal concentration of amino acids" that is sufficiently below the $K_m$, for methionine, for normal charging of methionyl-tRNA and thus allows incorrect charging of methionyl-tRNA with norleucine. Such reduction of the "low concentration of amino acids" to a "minimal concentration of amino acids" occurs at such a time so that the desired protein contains detectable incorporation of norleucine for methionine.

As used herein, "a high concentration of amino acids" is that concentration of amino acids which is in excess of the "low concentration of amino acids" and which cannot be reduced to the "minimal concentration of amino acids" prior to, at the time of, or shortly following induction of expression of the desired protein. For example, with the *E. coli* hosts and rbSt polypeptide of the specific examples, the "low concentration of amino acids" is less than about 0.50 mM each, as derived from a 0.1% yeast extract supplement. The "low concentration of amino acids" is reduced to a "minimal concentration of amino acids" which is less than about 0.05 mM each. Such amino acid concentrations are readily determined for any fermentation with any given host and any given polypeptide by quantitative amino acid analysis according to methods such as those of the specific examples.

Recombinant host microorganisms used in this invention are made by recombinant DNA techniques well known to those skilled in the art and set forth, for example, in Molecular Cloning, T. Maniatis, et al., Cold Spring Harbor Laboratory, (1982) and B. Perbal, A Practical Guide to Molecular Cloning, John Wiley & Sons (1984), which are incorporated herein by reference. Useful host microorganisms include any of the well known hosts suitable for cloning and expressing heterologous genes and including, for example, Bacillus, Saccharomyces and Streptomyces strains.

The heterologous polypeptide-producing recombinant microorganisms are cultivated in liquid nutrient medium. The medium comprises an excess of conventional nutrient materials that fulfill the cellular growth requirements of the microorganism, thereby enabling the microorganism to grow and multiply to a predetermined cellular density. This material includes sources of carbon, nitrogen and minerals such as sulfur, phosphorous, magnesium, potassium, copper, zinc, manganese and iron. Amino acids may be added in the form of protein hydrolysates usually made by subjecting naturally occurring proteinaceous materials, such as casein, soybean meal, lactalbumin, animal tissue, yeast cells and gelatin, to acid or enzymatic digestion. Mixtures of pure amino acids may also be added. We have found that norleucine biosynthesis and incorporation into expressed polypeptides occurs in fermentation media consisting of minimal media (e.g., defined inorganic salts and a carbon source, e.g., glucose or glycerol) either unsupplemented or supplemented with a low concentration of amino acids, and in which protein overexpression occurs. Oxygen is also provided to the medium. To achieve maximum cellular densities, the cultivation will usually be done in a way to enhance the area of the oxygen/liquid interface.

Important environmental factors affecting the cultivation include pH and temperature. The temperature will range between the minimum and maximum growth temperatures. Most bacteria exhibit maximum growth over a fairly narrow temperature range. For mesophilic bacteria, such as *E. coli*, the optimum temperature range is about 25° C. to about 42° C., preferably about 37° C. Most organisms will tolerate hydrogen ion concentrations ranging over several pH units. For bacteria, such as *E. coli*, the tolerable pH lies in the range of about 6 to 8, with about 6.8 being preferred.

If expression of a gene encoding a heterologous polypeptide is under control of a repressible expression control sequence, one can repress expression of that gene until a predetermined level of growth is reached by the cell culture by adding an appropriate repressor to the medium (e.g., tryptophan when expression is under control of the tryptophan promoter and operator).

After harvest, the cells are processed to recover the heterologous polypeptide. This normally involves disrupting the cells, separating crude heterologous polypeptide from bacterial proteins by one or more extraction steps, solubilizing the polypeptide (depending upon its hydrophobicity), oxidizing sulfhydryls to form proper disulfide bonds, when appropriate, and further purifying the polypeptide by gel filtration, high performance liquid chromatography or other protein purification procedures.

We have made a fermentation medium comprising low concentrations of amino acids which effectively supports overexpression of polypeptides in microorganisms and, in particular, heterologous polypeptides having the proper amino acid sequence (i.e., no norleucine substituted for methionine) in recombinant hosts, at a greatly reduced cost. This is important since it allows production of homogeneous products with attendant savings in product purification. Also facilitated is the expression of heterologous polypeptides linked by methionine residues that can be cleaved by cyanogen bromide.

On the other hand, it may be desirable to produce polypeptides having norleucine substituted for methionine. The purposeful replacement of methionine residues with norleucine makes available the synthesis of proteins with greater resistance to oxidation (to methionine sulfone or sulfoxide) and resistance to methionine-specific proteases or modifying reagents.

We have been running fermentations to produce heterologous polypeptides by recombinant microorganisms, for example, recombinantly-produced bovine somatotropin (rbSt) in *Escherichia coli* K-12 strains. These fermentations were initially conducted in a defined medium which was supplemented with relatively high concentrations of yeast extract (e.g., up to 5% wt/vol yeast extract). As a result of the relatively high concentrations of yeast extract employed, these initial fermentations were termed "high yeast extract" fermentations. However, the high cost of the yeast extract supplement, especially at the production scale, made these fermentations economically unfeasible. Accordingly, we developed a "low yeast extract" fermentation medium and process by supplementing with $\leq 0.5\%$ yeast extract.

When the low yeast extract fermentation medium was used, a major aberrant rbSt species (accounting for up to 30% of the total rbSt) was found upon reversed-phase high pressure liquid chromatography (RP-HPLC) analyses of isolated rbSt lots. No such aberrant rbSt species were detected in lots of rbSt produced during high yeast extract fermentations. Hence, the production of the newly encountered rbSt species was directly attributable to use of the cost effective low yeast extract fermentations.

The aberrant rbSt species were found to elute later than normal rbSt on RP-HPLC chromatograms and are called late-eluting rbSt (LE-rbSt). LE-rbSt was isolated and extensive structural analyses were performed. Structural data established that LE-rbSt is produced during low yeast extract fermentations as a result of substitution of norleucine for methionine at amino acid #124 in the rbSt molecule. Further norleucine substitutions at the other internal methionine positions, positions 5, 149 and 179, have also been detected, but do not appear to be directly responsible for the altered chromatographic behavior of rbSt upon RP-HPLC.

The incorporation of norleucine into rbSt during low yeast extract fermentations was unexpected, and the source of the norleucine was not known. Furthermore, it was not known why the low yeast extract fermentation protocol resulted in the incorporation of norleucine. Prior to this invention, there also were no known means for eliminating the incorporation of norleucine into rbSt. To overcome this problem, we supplemented the fermentation medium with L-methionine and thereby completely eliminated norleucine incorporation. Feedback inhibition of $\alpha$-isopropylmalate synthase (LeuA$^+$) by exogenous L-leucine also completely eliminated biosynthesis and accumulation of norleucine, and thus incorporation of norleucine into rbSt. The amount of methionine or leucine to be added to eliminate norleucine incorporation for any given host and desired polypeptide can readily be determined by the methods set forth in the examples. Supplementation with cysteine also decreased the amount of norleucine incorporated into the rbSt.

Native rbSt has a methionine residue at position #5. As with the other methionine residues, the position #5 methionine can be replaced by a norleucine residue. Although not wishing to be bound by theory, incorporation of norleucine at positions normally occupied by methionine residues is likely a direct result of charging of methionyl-tRNA with norleucine and subsequent interaction of the charged tRNA molecule with a methionine codon. Accordingly, replacement of a methionine codon with the codon for an amino acid other than methione would prevent norleucine incorporation into rbSt or other heterologous polypeptides having such methionine residues.

Bacterial cultures: *E. coli* strain BST-1 was used. This strain was derived from a wild-type strain of *E. coli* K-12 (ATCC e23716) by removal of the lambda prophage and the F plasmid and by introduction of the rpoH112 allele. This strain was then transformed with plasmid pURA4, a temperature-sensitive runaway replication plasmid vector derived from plasmids pBEU-17 and pBR322 and containing a gene encoding production of rbSt (U.S. patent application, Ser. No. 016,294, filed 19 Feb. 1987 and PCT patent application, PCT/US88/00328, incorporated herein by reference).

Culture Media: The defined media were based upon medium E of H. J. Vogel and D. M. Bonner, J. Biol. Chem., 218, pp. 97–106 (1955). The compositions and protocols for preparing the primary-seed and fermentation media are as follows:

| Primary-Seed Medium | |
| --- | --- |
| Components | Amount per liter |
| Na(NH$_4$)HPO$_4$.H$_2$O | 10.90 g |
| K$_2$HPO$_4$ | 2.61 g |
| Citric Acid.H$_2$O | 2.10 g |
| MgSO$_4$.7H$_2$O | 0.99 g |
| (NH$_4$)$_2$SO$_4$ | 0.66 g |
| Yeast Extract | 10.40 g |
| Glycerol | 5.00 g |
| R.O. water | |

For primary-seed cultures, the above components were hydrated with water (reverse-osmosis grade, R.O.) by q.s. to 1000 ml, and divided into 300-ml volumes prior to sterilization. Seed medium was sterilized for 20 minutes at 121° C. Following sterilization, the seed medium was allowed to cool, and 0.5 ml sterile ampicillin (25 g/liter in R.O. water titrated to pH 8.0 with NaOH and filter sterilized, 0.45 μm) was added.

| Fermentation Medium | |
| --- | --- |
| Components | Amount per liter |
| Na(NH$_4$)HPO$_4$.H$_2$O | 10.90 g |
| K$_2$HPO$_4$ | 2.61 g |
| Citric Acid (anhydrous) | 1.92 g |
| MgSO$_4$.7H$_2$O | 0.25 g |
| (NH$_4$)$_2$SO$_4$ | 0.66 g |
| Yeast Extract | 1.00 g |
| SAG4130 | 0.75 ml |
| R.O. water | |

The fermentation medium was prepared by increasing the amounts of the above components 200-fold and hydrating them in 165 liters of R.O. water in a 250-liter fermentor. The fermentation medium was then sterilized for 20 minutes at 121° C. (during sterilization, a medium volume increase of 20 liters was assumed, due to steam condensation). Following sterilization, the pH of the medium was checked to confirm a pH of 6.6 to 6.9. Upon cooling, two aseptic additions were made to complete the fermentation medium. The first addition consisted of a 200-ml aliquot of micronutrients (final concentrations: (NH$_4$)$_6$(MO$_7$)$_{24}$.4H$_2$O, 12 µM; H$_3$BO$_3$, 1.6 mM; COCl$_2$.6H$_2$O, 120 µM; CuSO$_4$, 39.9 µM; MnCl$_2$.4H$_2$O, 319 µM; ZnSO$_4$.7H$_2$O, 40.1 µM) which had been sterilized by filtration (0.45 µm). The second addition consisted of 15 liters cerelose (8.24 kg cerelose q.s. to 14 liters with R.O. water and adjusted to pH 4.0 with H$_2$SO$_4$). The fermentation medium was adjusted to pH 7.2 with 25% NaOH prior to inoculation.

The low yeast extract fermentation medium contained 0.1% yeast extract for BST-1 cultures. In some experiments, casamino acids, L-methionine, L-leucine, D,L-norleucine, food- or feed-grade sources of D,L-methionine, or L-cysteine was added to the fermentation medium.

Plasmid copy number assay: Crude plasmid copy number assays were done with culture samples which had been obtained periodically during the course of fermentations. Pellets containing about 2×10$^{10}$ bacteria from such samples were resuspended in 150 µl resuspension buffer (90 mM Tris, 90 mM borate, 60 mM EDTA, 25% sucrose). Lysozyme was added (30 µl of 10 mg/ml) and the suspension was incubated at 37° C. for 10 minutes, after which 30 µl ribonuclease A (20 mg/ml, preheated 10 minutes at 80° C.) was added. After 10 minutes at 37° C., 30 µl proteinase K (1 mg/ml) was added, and the incubation was continued for an additional 20 minutes. The mixtures were then shifted to 65° C. for 15 minutes. Cells were lysed by adding 210 µl lysis mixture (90 mM Tris, 90 mM borate, 60 mM EDTA, 1.25% (v/v) Triton X-100) and incubating them on ice for 15 to 20 minutes. The lysates were centrifuged 40 minutes in a microcentrifuge at 4° C. The cleared lysates were poured into clean 1.5 ml microcentrifuge tubes and stored at −20° C. Plasmid-containing lysates were typically analyzed by electrophoresis at 1 to 5 volts/cm in 0.8% agarose gels prepared in 90 mM Tris, 90 mM borate, 2.5 mM EDTA buffer.

EXAMPLE 1

Production of Norleucine Substituted rbSt by Use of a Low Yeast Extract Fermentation Medium Fermentation Protocol: Each primary-seed culture was inoculated with the contents of one culture ampoule (about 1 ml) and incubated at 28° C. to a culture density of 0.7 to 0.8 A$_{550}$. Following incubation, each primary-seed culture was placed on ice prior to use for inoculation of the fermentors. All primary-seed cultures were supplemented with ampicillin to yield cultures containing essentially all plasmid-bearing bacteria. BST-1 fermentations were initiated by inoculation with a 600-ml inoculum. Fermentor pH was controlled with anhydrous ammonia to maintain the pH at 7.2 to 7.4. Fermentor agitation and aeration rates were set at 320 rpm and 300 slm, at a backpressure of 10 psig. Culture growth was conducted at a permissive temperature of 27° C. BST-1 fermentations were maintained at 27° C. throughout, because plasmid runaway replication and rbSt synthesis were spontaneously induced.

Analytical Procedures: Culture aliquots were removed at various times from the primary seeds and fermentor and subjected to a series of analytical procedures to quantitate the culture density (absorbance at 550 nm), total bacterial dry weight, total rbSt concentration, glucose concentration, free ammonia concentration, acetate concentration, and microscopic identification and quantitation of inclusion bodies.

Sample Preparation for RP-HPLC: Samples were prepared for RP-HPLC isolation of the protein using an rbSt analysis preparation. A 10 A$_{550}$.ml aliquot of the fermentation culture was harvested by centrifugation and the supernatant was removed. The cell pellet was then resuspended in 650 µl of 6M guanidine hydrochloride containing 15 mg/ml dithiothreitol and boiled for 5 minutes. After the sample was cooled, 350 µl isopropanol was added.

RP-HPLC Isolation of rbSt: RP-HPLC was carried out on a Varian Vista 5500 liquid chromatograph with a 4.6×100 mm Bakerbond Widepore C-8 column. Gradient mobile phases were water versus isopropanol, each containing 0.1% trifluoroacetic acid (TFA). The flow rate was 1 ml/minute. The gradient ran from 35 to 54% B in 11 minutes. Detection was by UV at 215 nm. Aliquots of 500 µl of the samples were injected and the rbSt fractions were collected into 2 ml screw-cap microcentrifuge tubes. The samples were lyophilized, and stored at 4° C. These samples contained 1 to 3 nmoles of protein.

Sequencing of Polypeptides: N-terminal amino acid sequence analysis was performed on an Applied Biosystems (ABI) 470A Sequencer equipped with an on-line ABI 120A PTH analyzer. Initially, cartridge filters were prepared with 1.5 mg polybrene and precycled using the ABI program 03PRE. The samples were dissolved in 60 µl 0.1% TFA and loaded onto the filter in 30 µl aliquots. The filter was dried in the cartridge oven between applications. The ABI program 03CPTH was employed for at least 5 cycles on each sample. The percentage norleucine in the fifth cycle was calculated as the number of pmoles of norleucine divided by the total number of pmoles of norleucine plus methionine. The initial yield varied from 3.9 nmoles to 73 pmoles. The repetitive yields averaged 91.2% for the runs without carrier and 92.7% when carrier was used.

Amino Acid Analysis: To examine amino acid fluxes taking place in low yeast extract fermentations, medium samples were obtained periodically during fermentations and subjected to amino acid analysis. Amino-acid analysis was performed by the PTC method (R. L. Heinrikson and S. C. Meredith, Anal. Biochem., 136, pp. 65–74 (1984)), essentially as described by B. A. Bidlingmeyer, et al., J. Chromatogr., 336, pp. 93–104 (1984).

Fermentation medium samples were obtained from rbSt fermentations with strain BST-1 and subjected to amino acid analysis. Low yeast extract fermentations with strain BST-1 contained 0.1% yeast extract. The data in Table 1 show that, for a typical low yeast extract fermentation with strain BST-1, amino acids were present at initial concentrations ranging from 0.04 mM (histidine) to 0.38 mM (leucine), and that essentially all of the amino acids were exhausted prior to spontaneous induction of rbSt synthesis (about 15 hours post-inoculation). In fact, most amino acids were exhausted by about six hours post-inoculation. Alanine and glutamic acid reached minimum concentrations of 0.04 mM (15 hours post-inoculation) and 0.03 mM (17 hours post-inoculation), and increased to final concentrations of 0.88 mM and 1.65 mM, respectively. Accordingly, these data show that most of the amino acids were depleted from the medium approximately nine hours prior to spontaneous induction of rbSt synthesis. Furthermore, they show that amino acids required for culture growth and rbSt synthesis had to be synthesized de novo.

The data in Table 2 show the relationship between norleucine accumulation in the medium and incorporation of norleucine in rbSt. By 19 hours post-inoculation (about four hours post-induction), no norleucine was detected in the medium, while N-terminal amino acid sequencing revealed 2.6 mole-% norleucine already present at rbSt position #5 (Table 2). Fermentation samples obtained at 25 and 33.5 hours post-inoculation (about 10 and 18.5 hours post-induction) showed increasing concentrations of norleucine in the medium and correspondingly increasing fractions (mole-%) of norleucine incorporated at the N-terminus and position #5 of rbSt (Table 2). These results were also confirmed with a different *E. coli* host culture.

EXAMPLE 2

Synthesis and Excretion of Norleucine During Low Yeast Extract Fermentations with Strain BST-1

To demonstrate that norleucine was synthesized by *E. coli* cultures, fermentation medium samples were obtained during the course of low yeast extract fermentations (Example 1) and subjected to amino acid analysis. In particular, samples obtained from the low yeast extract fermentations with strain BST-1 were used. Samples of spent medium from these fermentations showed a temporal synthesis and accumulation of norleucine. Medium samples obtained 20 hours post-inoculation contained little detectable norleucine (9.02 minute elution time), while samples examined six hours later in the fermentation clearly demonstrated a norleucine peak (0.15 mM) on amino acid chromatographs. The norleucine peak continued to increase in samples obtained at 30 and 32 hours post-inoculation, reaching a final concentration of 0.47 mM.

The data collected show the time course for production of norleucine during a low yeast fermentation with strain BST-1. Norleucine synthesis and excretion started at 10 to 15 hours post-inoculation and continued until the end of the fermentation, reaching a final concentration of 0.60 mM. During one rbSt fermentation conducted with strain BST-1 and carried out for an extended period, the concentration of norleucine reached 2.47 mM by 66.2 hours post-inoculation. Therefore, we demonstrated that norleucine was synthesized de novo by the *E. coli* culture during low yeast extract fermentations. These results were also confirmed with a second *E. coli* strain.

The concentrations of available methionine and norleucine were also examined to understand the relationship between these two amino acids during a low yeast extract fermentation with strain BST-1. The data showed that the concentration of methionine supplied by the yeast extract supplement was typically <0.1 mM and that the methionine was depleted from the fermentation medium by 15 hours post-inoculation. From that point on in the fermentation, all of the methionine required for culture metabolism and growth, as well as rbSt synthesis, was synthesized by the culture. Concomitant with the depletion of methionine, the synthesis and accumulation of excess norleucine in the fermentation medium was observed. These data indicate that the rate of de novo synthesis of norleucine by the BST-1 culture was considerably greater than the rate of norleucine utilization (e.g., for protein synthesis).

EXAMPLE 3

Supplementation with Exogenous Amino Acids During Low Yeast Extract Fermentations In this Example we altered the concentrations of norleucine or other amino acids in the cytoplasmic amino acid pools, and observed the resulting effects on incorporation of norleucine into rbSt.

From the known amino acid composition of rbSt, an estimate of the amino acid requirement (per gram dry weight) for *E. coli* growth (J. L. Ingraham et al., Growth of the Bacterial Cell, pp. 108–10 and 122–25 (1983)), and the experimentally-determined amino acid composition of Difco casamino acids, we estimated that 3% casamino acid and 6 mM glycine should be added to a low yeast extract fermentation (Example 1) to supply all of the amino acids needed for cell growth and rbSt synthesis. With respect to methionine, this additional supplementation was calculated to represent 125% of the estimated amino acid requirement for cell growth and rbSt synthesis. When a low yeast extract fermentation supplemented with an additional 3% casamino acids and 6 mM glycine was conducted, no norleucine could be detected at the N-terminus of rbSt and only a trace (0.3 mole-%) of norleucine was detected at position #5 following N-terminal amino acid sequencing. In contrast, rbSt produced during an unsupplemented (no casamino acids) low yeast extract control fermentation contained 2.5 mole-% norleucine at the N-terminus and 15.3 mole-% norleucine at position #5. The amino acids in the additional casamino acids supplement prevented the incorporation of norleucine into rbSt. These data are in agreement with the observation that norleucine-containing rbSt (LE-rbSt) was not produced in fermentations containing high concentrations of yeast extract (e.g., 5% yeast extract).

EXAMPLE 4

Supplementation with Exogenous L-Methionine During Low Yeast Extract Fermentations Next we examined supplementation of the low yeast extract fermentations with 5 mM L-methionine. N-terminal amino acid sequencing of rbSt produced by strain BST-1 during an unsupplemented low yeast extract fermentation showed 2.1 and 22.1 mole-% norleucine at the N-terminus and position #5, respectively (Table 3). Supplementation of the low yeast extract fermentation medium with 8 mM D,L-norleucine further increased the levels of norleucine detected at the N-terminus and at position #5 (Table 3). Norleucine supplementation proved an effective means for enhancing the norleucine content in rbSt.

Supplementation with 5 mM L-methionine completely eliminated norleucine incorporation at rbSt position #5, while only a trace of norleucine (0.2 mole-%) was detected at the N-terminus. Detection of the trace of norleucine at the N-terminus of rbSt may have resulted from a reduced availability of formyl-methionine, due to methionine limitation, during the latter stages of the fermentation. Other fermentations conducted with methionine concentrations of $\geq 5$ mM have shown no norleucine at either the N-terminus or at position #5 of rbSt. Furthermore, titration experiments using L-methionine at concentrations as low as 1.25 mM have shown that norleucine incorporation into rbSt is reduced to <1 mole-% norleucine at position #5.

EXAMPLE 5

Supplementation with Other Sources of Methionine During Low Yeast Extract Fermentations This Example demonstrates that low yeast extract fermentations (Example 1) can be done, and norleucine incorporation into rbSt prevented, by supplementation with methionine sources that are less expensive than L-methionine.

An initial fermentation employing 5 mM D,L-methionine (Syntex Agri Business, Inc., Springfield, Mo.) was performed and was found to be effective for preventing norleucine incorporation into rbSt, as no norleucine could be detected at either the N-terminus or at position #5. Therefore, feed- and food-grades of D,L-methionine (Degussa Corp., Theodore, Ala.) were used at a concentration of 5 mM to supplement low yeast extract fermentations with strain BST-1. The data in Table 4 show that these two grades of D,L-methionine prevented incorporation of norleucine into rbSt. The food-grade D,L-methionine completely prevented incorporation of norleucine, while only a slight trace of norleucine (0.1 mole-%) was found at position #5 for rbSt produced during a fermentation supplemented with feed-grade D,L-methionine, presumably due to exhaustion of the 2.5 mM L-methionine component in the latter case (Table 4). In subsequent experiments, supplementation with $\geq 5$ mM feed-grade D,L-methionine completely prevented incorporation of norleucine into rbSt. Methionine supplementation, via either high levels of yeast extract, casamino acids, D,L-methionine or L-methionine, eliminated norleucine incorporation into rbSt.

EXAMPLE 6

Effect of Methionine on Norleucine Biosynthesis by Strain BST-1

To examine the effects of methionine supplementation on norleucine biosynthesis, norleucine synthesis and excretion by strain BST-1 during fermentations conducted with and without methionine supplementation were monitored. The data show that methionine supplementation did not prevent the synthesis of norleucine. Rather, methionine supplementation reduced the specific activity (mmoles norleucine/liter.hour.$A_{550}$) of norleucine biosynthesis for each of the samples examined. In fact, norleucine accumulated to a final concentration of 0.60 mM by the end of a low yeast extract fermentation conducted without methionine supplementation and 0.57 mM by the end of a companion fermentation with methionine supplementation. Methionine supplementation altered cell metabolism and enhanced culture growth, as mean oxygen-uptake (OUR) and carbon-dioxide evolution (CER) rates were 53% and 58% higher than those observed without methionine supplementation. Culture dry cell weight yields and final turbidities were also higher (24% and 38%, respectively) with methionine supplementation.

EXAMPLE 7

Relationship Between rbSt Synthesis and Norleucine Biosynthesis and Excretion Culture aliquots were obtained during low yeast extract fermentations with strain BST-1 and the amino acids were analyzed and total rbSt quantitated. The data show that by 15 hours post-inoculation the methionine concentration in the medium was reduced from 0.05 to 0.00 mM. Shortly after 15 hours post-inoculation norleucine biosynthesis began, reaching a final concentration of 0.86 mM by 40 hours post-inoculation. Spontaneous induction of rbSt synthesis occurred at the same time that norleucine biosynthesis and excretion started. These data suggested that the synthesis and accumulation of rbSt by the $E.$ $coli$ culture may have been responsible for mediating the biosynthesis of norleucine so we tested this.

Production of rbSt by BST-1 cultures follows spontaneous induction of plasmid runaway replication. Accordingly, we examined norleucine biosynthesis by a culture capable of both runaway plasmid replication and rbst synthesis (BST-1), a culture capable of plasmid runaway replication without rbSt synthesis (BST-1C which contains plasmid pURA4 $\Delta bgh_{E/H}$ derived from pURA4 (United States patent application 016,294) and capable of runaway replication, but unable to synthesize rbSt due to an 850 bp ScoRI/HindIII deletion of most of the rbSt gene), and a culture having neither runaway plasmid replication nor rbSt synthesis (strain BST-1C, an isogenic plasmid-free derivative of strain BST-1 which grows independently of runaway plasmid replication and rbSt synthesis). The data in Table 5 show that strains BST-1C and BST-1C (pURA4 $\Delta bgh_{E/H}$) grew to densities (dry weight) which were 2.2 to 2.5-fold greater than BS-1. These data also show that strains BST-1C and BST-1C (pURA4 $\Delta bgh_{E/H}$) synthesised essentially equivalent amounts of norleucine (about 0.01 mmoles norleucine/g dry cell weight) during their low yeast extract fermentations. However, strain BST-1 synthesised considerably more norleucine (about 14-fold higher) than either of the other strains examined, reaching a mean concentration of 0.14 mmoles norleucine/g dry cell weight (Table 5). We also confirmed that both plasmid-bearing strains had runaway plasmid replication.

Collectively, these data show that norleucine biosynthesis by $E.$ $coli$ was correlated with rbSt synthesis during low yeast extract fermentations. Independent of the phenomenon of plasmid runaway replication, appreciable norleucine accumulation was not observed without rbSt synthesis. Although somewhat inefficient, norleucine was produced by $E.$ $coli$ strains during low yeast extract fermentations that were not expressing heterologous polypeptides.

EXAMPLE 8

Leucine Supplementation to Eliminate Norleucine Incorporation During Protein Synthesis In this Example, we examined the relationship between exogenous leucine, and other amino acids, in the low yeast extract supplement and biosynthesis and incorporation of norleucine into rbSt.

Amino acid analysis of fermentation media samples revealed essentially all the exogenous leucine was depleted (initially 0.27 mM reduced to 0.03 mM) by 14 hours post-inoculation, a point during the fermentation corresponding very nearly to the time at which norleucine biosynthesis and excretion began.

Additional fermentations were performed to directly examine the effects of leucine supplementation on norleucine biosynthesis and excretion, as well as on incorporation of norleucine into rbSt. The data showed that, without leucine supplementation of the low yeast extract fermentation, norleucine biosynthesis and excretion began about 15 hours post-inoculation, reaching a final concentration of 0.86 mM by 40 hours post-inoculation. Supplementation of a second fermentation with 15 mM L-leucine resulted in a complete inhibition of norleucine biosynthesis and excretion. Feedback inhibition of α-isopropylmalate synthase by exogenous leucine prevented norleucine biosynthesis by blocking the initial reaction in the pathway leading to norleucine biosynthesis. The data showed that growth of a leucine-supplemented culture was indistinguishable from that of an unsupplemented culture for the first 19 hours post-inoculation. After that point, growth of the leucine-supplemented culture began to cease, reaching a final density of 11.4 $A_{550}$ as compared with 24.4 $A_{550}$ for the unsupplemented culture. When data for production of rbSt by the leucine-supplemented and unsupplemented cultures were compared, rbSt production by the leucine-supplemented culture began declining at 20 hours post-inoculation. Initial rates of rbSt synthesis for the leucine-supplemented and unsupplemented cultures were very similar (k=0.66 and 0.78 hours$^{-1}$, respectively), indicating no initial perturbation by leucine supplementation. Amino acid analysis of samples of fermentation media obtained from these fermentations confirmed no norleucine was synthesized by the leucine-supplemented culture, while the final norleucine concentration reached 0.60 mM for the unsupplemented culture.

N-terminal amino acid sequencing of rbSt samples obtained from the unsupplemented and 15 mM L-leucine-supplemented fermentations showed 1.3 and 22.0 mole-% norleucine at the N-terminus and position #5 of rbSt from the unsupplemented fermentation, while no norleucine was detected at either position for rbSt obtained from the L-leucine-supplemented fermentation (Table 6).

EXAMPLE 9

Effects of L-Cysteine Supplementation on Norleucine Incorporation into rbSt

Fermentations either unsupplemented or supplemented with 5 or 15 mM L-cysteine were conducted. The biosynthesis and excretion of norleucine and incorporation of norleucine into rbSt were monitored to determine whether such supplementation could reduce the biosynthesis of norleucine and reduce its incorporation into rbSt. The data in Table 7 show that some norleucine was synthesized by strain BST-1 even when supplemented with exogenous cysteine. The slight reduction in the concentration of norleucine detected in the extracellular medium during fermentations supplemented with 15 mM L-cysteine was likely due to a perturbation of growth at the highest cysteine level. The mean final culture absorbance ($A_{550}$), total dry weight, and rbSt yield for the 15 mM L-cysteine supplemented cultures were 51%, 48%, and 45% of the respective levels obtained for cultures from unsupplemented fermentations. Supplementation with 5 mM L-cysteine did not appreciably alter the growth of the culture, compared with the unsupplemented fermentation, and no reduction in the amount of norleucine was detected (Table 7). Supplementation with 5 mM L-cysteine did, however, reduce the amount of norleucine detected at the N-terminus and at position #5 of rbSt from 1.7 and 21.8 mole-% to 1.6 and 18.9 mole-%, respectively (Table 7). Supplementation with 15 mM L-cysteine further reduced the concentration of norleucine at the N-terminus and at position #5 to 1.1 mole-% and 13.8 mole-%, respectively.

Fermentations were also conducted with strain BST-1C (pURA4C-S). Plasmid pURA4C-S was derived from pURA4 by site-directed mutagenesis, replacing each of the four internal cysteine residues of rbSt with serine residues. Synthesis of rbSt by this strain proceeded without any demand upon de novo synthesized cysteine for rbSt synthesis. By the end of an unsupplemented low yeast extract fermentation with strain BST-1C (pURA4C-S), norleucine had accumulated to an extracellular concentration of 0.43 mM. Furthermore, N-terminal amino acid sequencing revealed 0.9 and 17.7 mole-% norleucine at the N-terminus and position #5 of rbSt, respectively.

Neither cysteine supplementation nor synthesis of rbSt which was void of cysteine greatly affected synthesis of norleucine, but they did slightly enhance methionine levels. The enhanced availability of methionine resulted in a more effective competition with norleucine for correct charging of tRNA$^{Met}$ and tRNA$^{fMet}$. Furthermore, the result of the enhanced methionine biosynthesis was a dose-dependent reduction of norleucine incorporation into rbSt.

EXAMPLE 10

Use of Mutant Microorganisms that Overproduce Methionine to Eliminate Incorporation of Norleucine into Heterologous Polypeptides Expressed Thereby It is also possible to eliminate the incorporation of norleucine into heterologous polypeptides by using microorganisms that overproduce methionine as hosts for expressing the polypeptides. Such mutants include either feedback-insensitive homoserine transsuccinylase (metA) mutants, or mutants derepressed for methionine (metJ or metK mutants), or both (R. J. Rowbury, In: Amino Acids Biosynthesis and Genetic Regulation, K. M. Herrman and R. L. Somerville, eds., pp. 191–211 (1983)). Methionine-prototrophic organisms are exposed to ultraviolet irradiation or to a chemical mutagen (e.g., methylmethane sulfonate or 1-methyl-3-nitro-1-nitrosoguanidine) at a dose sufficient to result in 75–90% killing, and dilutions are inoculated onto plates of defined media supplemented with α-methyl methionine, ethicnine, or norleucine. An alternative approach, employing selection for resistance to microcins 15, 93 or 136 may also be employed to yield methionine overproducers (F. Baquero, et al., J. Bacteriol., 135, pp. 342–347, (1978)). A further alternative for obtaining metA, metJ, and metK mutants involves the introduction of known mutant methionine alleles (e.g., metA::Tn10, etc., available from the E. coli Genetic Stock Center, Yale University, c/o B. J. Bachmann) by standard transductional approaches (J. H. Miller, In: Experiments in Molecular Genetics, pp. 201–205, Cold Spring Harbor Laboratories (1971)). From either protocol, putative clones are tested for methionine overproduction (and excretion) in cross-feeding experiments by overlaying colonies of such clones, previously grown on plates of methionine-free defined medium, with a top-agar layer which is inoculated with a non-reverting methionine-auxotrophic bacterium as an indicator. Following incubation, growth of the methionine-auxotroph is observed over and around colonies which overproduce and excrete methionine. Quantitation of total cell methionine content (per gram dry weight) and methionine content in the extracellular milieu (cell-free spent medium) is accomplished following growth in defined liquid medium by methods of quantitative amino acid analysis such as are set forth in the examples above. Low yeast extract fermentations (without methionine supplementation) performed with such methionine-overproducing strains transformed with a heterologous gene by known techniques result in the prevention of norleucine incorporation into heterologous polypeptides.

EXAMPLE 11

Increased Oxidation Stability of rbSt Containing Norleucine Substituted for Methionine Increased stability against oxidation of rbSt in which methionine has been replaced by norleucine was demonstrated by exposing the protein to 3% $H_2O_2$ and subsequent analysis by reversed-phase HPLC (RP-HPLC). Upon exposure to $H_2O_2$, native rbSt (norleucine-free) shifted to two earlier elution positions following RP-HPLC. The first position shift occurred very rapidly (half-life ca. 1.2 minutes) and caused modified rbSt molecules to elute slightly earlier than rbSt that had not been exposed to $H_2O_2$, due to modification at site A of the molecule. The second position shift occurred more slowly (half-life ca. 14.3 minutes) and resulted in a larger RP-HPLC shift, due to modification at site B of the molecule. (Sites A and B have been arbitrarily designated to represent two of the four methionine residues present in the native rbSt molecule.)

Native rbSt (norleucine-free) and norleucine-substituted (ca. 36% norleucine at rbSt positions 5, 124, 149 and 179) rbSt, obtained from methionine- and norleucine-supplemented fermentations, respectively, were exposed to 3% $H_2O_2$ in 5 mM $(NH_4)_2CO_3$, pH 10.0 at 2 mg rbSt/ml at room temperature. Following exposure, the $H_2O_2$ was removed by gel filtration on a Pharmacia PD-10 G-25 column equilibrated in the same buffer. Samples were then analyzed by RP-HPLC. After 40 minutes exposure, native rbSt exhibited 100% and 85.6% modification of sites A and B, respectively, while norleucine-substituted rbSt contained only 47.6% and 51.4% modification of these sites. Therefore, the replacement of methionine by norleucine conferred enhanced oxidation stability upon the rbSt molecule, as determined by RP-HPLC behavior.

EXAMPLE 12

Replacement of Methionine Codons in rbSt Gene to Prevent Incorporation of Norleucine Translation of the messenger RNA transcript for the native rbSt gene results in incorporation of a methionine residue at position #5. As with other positions normally occupied by methionine residues in rbSt, position five can be replaced by a norleucine residue. Accordingly, replacement of a methionine codon with the codon for an amino acid other than methione would prevent norleucine incorporation into rbSt.

By incorporation of a synthetic oligonucleotide according to techniques well known to those skilled in the art (U.S. Ser. No. 07/299,107, filed 19 Jan. 1989), the methionine codon, ATG, at position #5 in a gene encoding rbSt was changed to ATC, which encodes isoleucine, resulting in production of a construct designated rbSt mO. Growth of, and rbSt synthesis by, an *E. coli* host bearing a vector with this gene were monitored during a stirred-tank fermentation in low yeast extract medium at the 250-liter scale. Fermentation medium samples were obtained during the course of the fermentation and subjected to amino acid analysis. In addition, rbSt was isolated and subjected to N-terminal amino acid sequencing to quantitate the amino acid residue found at position #5. Norleucine was produced during the fermentation and accumulated to a final concentration of 0.36 mM extracellularly by the end of the fermentation. N-terminal amino acid sequencing of the rbSt encoded by the mO gene revealed only isoleucine, and not norleucine or methionine, was present at position #5. Therefore, replacement of the methionine codon at position #5 with the codon for isoleucine prevented norleucine incorporation.

Similarly, replacement of methionine codons at other positions in the rbSt molecule would prevent norleucine incorporation into rbSt. X-ray crystallographic analysis indicates that methionine residue #5 is in a portion of the bSt with little defined secondary structure, residues 124 and 179 are in alpha helices, and 149 is in a region of chain reversal, morst likely a β-turn (S. S. Abdel-Meguid, et al, Proc. Natl. Acad. Sci. USA, 84, pp. 6434–37 (1987)). The Chou and Fasman predictive parameters correctly predict the secondary structure around residues 5, 124 and 149, but wrongly suggest that residue 179 is in a region of β-pleated sheet (P. Y. Chou and G. D. Fasman, Ann. Rev. Biochem., 47, pp. 251–76 (1978); C.-J. H. Chen and M. Sonenburg, Biochem., 16, pp. 2110–18 (1977)).

Analysis of the amino acid sequences of bovine (L. Graf and C. H. Li, Biochem. Biophys. Res. Comm., 56, pp. 168–76 (1974)), porcine (P. H. Seeburg, et al, DNA, 2, pp. 37–45 (1983)), ovine (C. H. Li, et al, Int. J. Pep. Pro. Res., 4, pp. 151–53 (1972)), equine (M. M. Zakin, et al, Int. J. Pep. Pro. Res., 8, pp. 435–44 (1976)), rat (G. S. Page, et al, Nucl. Acids Res., 9, pp. 2087–2104 (1981)), human (F. M. DeNoto, et al, Nucl. Acids Res., 9, pp. 3719–30 (1981)), monkey (C. H. Li, et al, Arch. Biochem. Biophys., 245, pp. 287–91 (1986)), and chicken (L. M. Souza, et al, J. Exp. Zool., 232, pp. 465–73 (1984)) somatotropins indicates that the methionine at position 5 in bSt, pSt, oSt, eSt, rat St and chicken St is isoleucine in human and monkey somatotropin. The amino acid sequences of trout (L. B. Agellon and T. T. Chen, DNA, 5, pp. 463–71 (1986)) and salmon S. Sekine, et al, European patent application No. 85107987.1) are quite divergent from mammalian and chicken St, and an alignment of their sequences is difficult in this region.

The methionine at position 124 is invariant in the seven mammalian and chicken somatotropins.

The methionine at position 149 in bovine, ovine, and rat St is leucine in porcine, horse, and chicken St and serine in human and monkey St. The corresponding amino acid in trout and salmon St is most likely leucine. Since the amino acid sequence of threonine-asparagine-serine for residues 147–149 of human and monkey St is identical to the 98–100 of bSt and pSt, in which isoaspartic acid formation and chain cleavage occur, changing methionine 149 to serine may lead to the same type of cleavage.

The methionine at position 179 in bSt, pSt, oSt, rat St and chicken St is valine in human and monkey St and alanine in trout and salmon St.

There are four additional positions in the amino acid sequences of mammalian and chicken somatotropins in which an amino acid other than methionine occurs in bSt, and methionine is found in St from another species. The valine at position 15 in bSt, pSt, oSt, eSt, rat St and chicken St is methionine in human and monkey somatotropins. The leucine at position 73 in bSt, oSt, hSt, and monkey St is valine in pSt and methionine in horse, rat, and chicken St. The valine at position 102 in bSt, pSt, oSt, St, hSt, monkey and chicken St is methionine in rat St. Lastly, the leucine at position 169 in bSt, pSt, oSt, eSt, rat and chicken St is methionine in human and monkey St.

Among the non-methionine/methionine substitutions in mammalian and chicken somatotropins, valine substitutes for methionine at 4 positions and in 16 instances (instance= number of positions+number of species with valine at that positon), leucine and methionine are interchangeable at 3 positions and 13 instances, and isoleucine substitutes for methionine at 1 position and 2 instances.

Considering the foregoing, if the four methionine-containing sites in bSt are considered independently, the preferred change for position 5 is to isoleucine as set forth above and also for the invariant methionine at position 124. Valine is also preferred. Leucine is preferred for position 149. Valine is preferred for position 179.

If all four methionines residues in bSt are changed to a single identical amino acid, the preference is 1) leucine, 2) valine, or 3) isoleucine.

Following a similar analysis, other appropriate amino acid replacements for methionine in other heterologous polypeptides can also be chosen by those skilled in the art.

EXAMPLE 13

Effects of Supplementation with Leucine, Isoleucine, and Valine on Fermentations to Produce Recombinant Bovine Somatotropin Supplementation of low yeast extract fermentations with L-leucine completely inhibited the synthesis of norleucine by strain BST-1. In addition, such fermentations yielded rbSt which, when subjected to N-terminal amino acid sequencing, did not contain norleucine at position number five of the rbSt molecule. However, supplementation of low yeast extract fermentations with L-leucine alone perturbed culture growth and reduced the total amount of rbSt produced.

To obviate any inhibition of culture growth potentially mediated by L-leucine supplementation on the de novo synthesis of isoleucine and/or valine, fermentations were conducted employing supplementation with L-leucine, L-isoleucine, and L-valine. Supplementation with each of the three amino acids greatly enhanced culture growth when compared to a parallel fermentation supplemented with only L-leucine (culture densities of 44.9 and 12.9 $A_{550}$, respectively). In addition, supplementation with leucine, isoleucine, and valine resulted in a final rbSt titer of 1.97 grams rbSt/liter, compared with only 0.43 grams rbSt/liter from a leucine-supplemented fermentation. N-terminal amino acid sequencing data revealed no norleucine was present at position number five for rbSt obtained from either low yeast extract fermentation. Furthermore, quantitative amino acid analyses detected no norleucine in any fermentation medium samples for either fermentation. Collectively, these data support the observation that L-leucine supplementation of low yeast extract fermentations for the production of rbSt inhibits the de novo synthesis of norleucine and its incorporation into the rbSt molecule.

TABLE 1

Amino Acid Concentrations in Fermentation Medium Samples Obtained Prior to Inoculation and at the Time of Spontaneous Induction of rbSt Synthesis During a BST-1 Fermentation[a]

| Amino Acid | Amino Acid Concentration (mM)[b] | |
|---|---|---|
|  | Initial | At Induction |
| Alanine | 0.35 | 0.04 |
| Arginine | 0.07 | 0.00 |
| Asparagine | 0.06 | 0.00 |
| Aspartic Acid | 0.10 | 0.00 |
| Cysteine | nd[c] | nd |
| Glutamine | 0.16 | 0.03 |
| Glutamic Acid | 0.16 | 0.03 |
| Glycine | 0.13 | 0.00 |
| Histidine | 0.04 | 0.00 |
| Isoleucine | 0.23 | 0.00 |
| Leucine | 0.38 | 0.03 |
| Lysine | 0.03 | 0.02 |
| Methionine | 0.07 | 0.00 |
| Phenylalanine | 0.19 | 0.00 |
| Proline | 0.16 | 0.03 |
| Serine | 0.13 | 0.00 |
| Threonine | 0.13 | 0.00 |
| Tryptophan | 0.05 | 0.00 |
| Tyrosine | 0.06 | 0.03 |
| Valine | 0.28 | 0.03 |

[a]rbSt synthesis spontaneously induced about 15 hours post-inoculation.
[b]The fermentation medium was prepared by supplementation with 0.1% (wt/vol) yeast extract. Glutamine and glutamic acid concentrations shown are 50% of quantitated glutamine + glutamic acid (Glx).
[c]Not determined.

TABLE 2

Relationship Between Norleucine Biosynthesis and Excretion and Incorporation of Norleucine into rbSt Synthesized During an Unsupplemented Low Yeast Extract Fermentation

| Time (Hours Post-Inoculation)[a] | Norleucine Incorporation (Mole-%) | | Norleucine Concentration (mM) |
|---|---|---|---|
|  | N-Terminus | Position #5 |  |
| 19.0 | 0.0 | 2.6 | 0.0 |
| 25.0 | 1.4 | 18.3 | 0.1 |
| 33.5 | 2.0 | 24.9 | 0.6 |

[a]Spontaneous induction of rbSt synthesis occurred at approximately 15 hours post-inoculation.

TABLE 3

Effects of Supplementation with D,L-Norleucine or L-Methionine on Incorporation of Norleucine at the N-Terminus and Position #5 of rbSt During Fermentations with Strain BST-1[a]

| Medium Supplementation[b] | Norleucine Incorporation (Mole-%) | |
|---|---|---|
|  | N-Terminus | Position #5 |
| Unsupplemented | 2.1 | 22.1 |
| 8 mM D,L-Norleucine | 4.4 | 34.3 |
| 5 mM L-Methionine | 0.2 | 0.0 |

[a]Fermentation samples harvested at 30 hours post-inoculation.
[b]All media were supplemented with 0.1% yeast extract in addition to the above indicated supplements.

TABLE 4

Effects of Supplementation with Feed- and Food-Grades of D,L-Methionine on Incorporation of Norleucine at the N-Terminus and Position #5 of rbSt During Fermentations with Strain BST-1[a]

| Medium Supplementation[b] | Norleucine Incorporation (Mole-%) | |
|---|---|---|
|  | N-Terminus | Position #5 |
| Unsupplemented | 2.04 | 24.91 |
| 5 mM L-Methionine | 0.00 | 0.00 |
| 5 mM D,L-Methionine, Feed-Grade[c] | 0.00 | 0.07 |
| 5 mM D,L-Methionine, Food-Grade | 0.00 | 0.00 |

[a]Fermentation samples harvested at 31 hours post-inoculation.
[b]All media were supplemented with 0.1% yeast extract in addition to the above indicated supplements.
[c]Feed- and food-grade sources of D,L-methionine were obtained from Degussa Corp.

TABLE 5

Relationship Between Norleucine Biosynthesis and Excretion and Synthesis of rbSt by Strain BST-1[a]

| Strain | Plasmid | Dry Weight (g/liter) | Norleucine Concentration (mM) | Norleucine Concentration (mM/g dry wt) |
|---|---|---|---|---|
| BST-1 | pURA4 | 5.4 | 0.73 | 0.14 |
| BST-1C | none | 13.3 | 0.09 | 0.01 |
| BST-1C | pURA4 Δbgh$_{E/H}$ | 11.7 | 0.12 | 0.01 |

[a]Fermentations were each conducted in duplicate and data are shown as mean values. Fermentation media were supplemented with 0.1% yeast extract.

TABLE 6

Effects of L-Leucine Supplementation on Incorporation of Norleucine at the N-Terminus and Position #5 of rbSt During Fermentations with Strain BST-1[a]

| Medium Supplementation[b] | Norleucine Incorporation (Mole-%) | |
|---|---|---|
|  | N-Terminus | Position #5 |
| Unsupplemented | 1.3 | 22.0 |
| 15 mM L-Leucine | 0.0 | 0.0 |

[a]Fermentation samples harvested at 40 and 46 hours post-inoculation, for the unsupplemented and leucine-supplemented fermentations, respectively.
[b]Fermentation media were supplemented with 0.1% yeast extract in addition to the supplement indicated above.

TABLE 7

Effects of L-Cysteine Supplementation on Norleucine Biosynthesis and Excretion and Incorporation of Norleucine into rbSt[a]

| Medium Supplementation[b] | Norleucine Concentration (mM) | Norleucine Incorporation (Mole %) | |
|---|---|---|---|
|  |  | N-Terminus | Position #5 |
| unsupplemented | 0.73 | 1.7 | 21.8 |
| 5 mM L-cysteine | 1.18 | 1.6 | 18.9 |
| 15 mM L-cysteine | 0.59 | 1.1 | 13.8 |

[a]Fermentation samples were harvested at 40 hours post-inoculation.
[b]Fermentation media were supplemented with 0.1% yeast extract in addition to the supplements indicated above.

CHART 1

Amino Acid Sequence Of Bovine Somatotropin

```
1
ala phe pro ala met ser leu ser gly leu phe ala asn ala val
                    20
leu arg ala gln his leu his gln leu ala ala asp thr phe lys
                                            40
glu phe glu arg thr tyr ile pro glu gly gln arg tyr ser ile gln asn thr gln val ala phe cys phe ser glu thr ile pro ala pro thr gly lys asn glu ala gln gln lys ser asp leu glu leu
                    80
leu arg ile ser leu leu leu ile gln ser trp leu gly pro leu
                                            100
gln phe leu ser arg val phe thr asn ser leu val phe gly thr ser asp arg val tyr glu lys leu lys asp leu glu glu gly ile leu ala leu met arg glu leu glu asp gly thr pro arg ala gly
                    140
gln ile leu lys gln thr tyr asp lys phe asp thr asn met arg
                                            160
ser asp asp ala leu leu lys asn tyr gly leu leu ser cys phe arg lys asp leu his lys thr glu thr tyr leu arg val met lys
                                            190
cys arg arg phe gly glu ala ser cys ala phe
```

We claim:

1. A method for producing norleucine comprising growing *E. coli* on a fermentation medium having a low concentration of amino acids and then isolating the norleucine produced by said *E. coli*.

* * * * *